United States Patent
Gauthier et al.

(10) Patent No.: US 11,391,232 B2
(45) Date of Patent: Jul. 19, 2022

(54) PARTICULATE MATTER SENSOR

(71) Applicant: DELPHI TECHNOLOGIES IP LIMITED, St. Michael (BB)

(72) Inventors: Daniel G. Gauthier, Clarkston, MI (US); David D. Cabush, Howell, MI (US); Alfredo Ibarra Covarrubias, Oxford, MI (US); David A. Goulette, Marine City, MI (US)

(73) Assignee: DELPHI TECHNOLOGIES IP LIMITED, St. Michael (BB)

( * ) Notice: Subject to any disclaimer, the term of this patent is extended or adjusted under 35 U.S.C. 154(b) by 450 days.

(21) Appl. No.: 16/661,494

(22) Filed: Oct. 23, 2019

(65) Prior Publication Data

US 2021/0123392 A1    Apr. 29, 2021

(51) Int. Cl.
*G01N 33/00* (2006.01)
*F02D 41/14* (2006.01)
*G01N 27/16* (2006.01)

(52) U.S. Cl.
CPC ..... *F02D 41/1466* (2013.01); *G01N 33/0036* (2013.01); *G01N 27/16* (2013.01)

(58) Field of Classification Search
CPC .......... F02D 41/1466; F02D 2041/281; G01N 33/0036; G01N 27/16; G01N 15/0606; G01N 15/0656; G01N 2015/0046; Y02A 50/20

See application file for complete search history.

(56) References Cited

U.S. PATENT DOCUMENTS

| | | | |
|---|---|---|---|
| 4,147,513 A | | 4/1979 | Bienkowski et al. |
| 4,300,990 A | * | 11/1981 | Maurer ............. G01N 27/4071 |
| | | | 204/426 |
| 7,609,068 B2 | | 10/2009 | Ripley |
| 8,249,827 B2 | | 8/2012 | Nelson et al. |
| 8,860,439 B2 | * | 10/2014 | Kimata ............. G01N 15/0656 |
| | | | 324/464 |
| 8,928,388 B2 | | 1/2015 | Lu et al. |
| 2008/0282769 A1 | | 11/2008 | Nelson |
| 2008/0283398 A1 | | 11/2008 | Nelson et al. |
| 2009/0139081 A1 | | 6/2009 | Nelson |
| 2012/0103059 A1 | * | 5/2012 | Kimata ............. G01N 15/0656 |
| | | | 29/25.42 |
| 2015/0014163 A1 | | 1/2015 | Soyez et al. |
| 2015/0177204 A1 | * | 6/2015 | Bessen ................ G01M 15/102 |
| | | | 73/114.71 |
| 2018/0335398 A1 | | 11/2018 | Covarrubias et al. |
| 2022/0003705 A1 | * | 1/2022 | Herweg ............. G01N 33/0006 |

* cited by examiner

*Primary Examiner* — Freddie Kirkland, III
(74) *Attorney, Agent, or Firm* — Joshua M. Haines

(57) ABSTRACT

A particulate matter sensor includes a first sensing electrode and a second sensing electrode spaced away from the first sensing electrode such that an electrode gap is formed between the first sensing electrode and the second sensing electrode upon which particulate matter is collected, thereby changing conductance between the first sensing electrode and the second sensing electrode. An ionic conductive material is in electrical communication with the first sensing electrode and the second sensing electrode.

13 Claims, 6 Drawing Sheets

PARTICULATE MATTER SENSOR

TECHNICAL FIELD OF THE INVENTION

This application relates to a particulate matter sensor with features which permit diagnosis thereof.

BACKGROUND OF INVENTION

Soot sensors, also known as particulate matter (PM) sensors, are often used in vehicles having diesel engines. A particulate matter sensor may be located upstream from a particulate filter, where the sensor is exposed to exhaust flow from the engine having soot particles entrained in the exhaust gas. Alternatively, a particulate matter sensor may be located in a gas stream downstream from a particulate filter, where the sensor is used to monitor the proper operation of the particulate filter.

A known method of sensing soot uses a particulate matter sensor having two electrodes that are spaced from one another. In the absence of soot, there is very low electrical conductivity between the electrodes. As soot accumulates on the surface of the sensor, soot particles act to bridge the gap between the electrodes. Because the soot particles are electrically conductive, the conductivity between the electrodes increases, and this change in conductivity can be related to the amount of soot in the gas stream. Sensors that operate according to this principle are disclosed in U.S. patent application Ser. No. 11/749,262 published as US Patent Application Publication 2008/0283398, U.S. patent application Ser. No. 11/750,883 published as US Patent Application Publication 2008/0282769, and U.S. patent application Ser. No. 11/998,238 published as US Patent Application Publication 2009/0139081, the contents of all of which are hereby incorporated by reference in their entirety.

Government regulations require that the particulate matter sensor has self diagnostics (i.e. On Board Diagnostics or OBD) capability to verify that it is functioning properly. However, with a normally open circuit device, and soot normally not present, this can be difficult. The sensor must be able to verify that the circuit is functioning properly and that if a conductive material lands on the electrode, the sensor can detect it. In a conventional sensor as described, a "clean" sensor, that is a sensor with no accumulated soot, will appear electrically as an open circuit. The same open circuit indication may result from a damaged sensor or a disconnected wiring harness.

In order to provide self diagnostics, U.S. Pat. No. 8,928,388 to Nelson et al., the disclosure of which is incorporated herein by reference in its entirety, provides a soot sensor with a bias resistor electrically connected between the two electrodes. In the absence of particulate matter, the resistance of the sensor will be at its maximum and will essentially equal the resistance of the bias resistor. Under this condition, the voltage measured across the two electrodes will be:

$$V_{measured} = V_{supply} \frac{R_{bias}}{R_{pullup} + R_{bias}}$$

where $V_{supply}$ is the voltage of the voltage supply, $R_{bias}$ is the resistance of the bias resistor, and $R_{pullup}$ is the resistance of a pull-up resistor which is connected in series between the voltage supply and the bias resistor. This value represents the highest voltage that should be present in a properly connected, undamaged sensor. In an example where $R_{bias}$ is equal to 10 megaohms and $R_{pullup}$ is equal to 1 megaohm, the voltage measured in the absence of particulate matter would be about 91 percent of the supply voltage $V_{supply}$. A voltage below this level would be indicative of accumulating particulate matter between the two electrodes.

Several fault conditions may occur in a particulate matter sensing system that would appear as an open circuit. For example, an electrical connector may become disconnected; wire in a wiring harness may break, or damage may occur to the sensing element portion resulting in a break in a conductor. Any of these fault conditions would result in $V_{measured}$ being essentially $V_{supply}$, which is higher than the highest voltage that would be present in a properly connected system (for example 91% of $V_{supply}$ with $R_{pullup}=1$ megaohm and $R_{bias}=10$ megaohms). A voltage in excess of the maximum voltage expected from a properly connected undamaged sensor can be used to indicate the presence of a fault condition.

While the arrangement of Nelson et al. may be effective for diagnosing the sensor, implementation of the bias resistor can add significant cost. The sensing element is effectively a multi-layer ceramic element which needs to be sintered. However, the bias resistor may be made of ruthenium oxide or similar resistive materials with a glass coating which must be sintered at a lower temperature than the other portions of the sensing element, and as a result, must be applied to, and sintered after, the remainder of the sensing element has been sintered. Since a separate sintering process is required for the bias resistor, additional manufacturing time and cost is required.

What is needed is a particulate matter sensor which minimizes or eliminates one or more of the foregoing deficiencies.

SUMMARY OF THE INVENTION

Briefly described, a particulate matter sensor in accordance with the present disclosure is provided for detecting particulate matter is a gas stream. The particulate matter sensor includes a first sensing electrode and a second sensing electrode spaced away from the first sensing electrode such that an electrode gap is formed between the first sensing electrode and the second sensing electrode upon which particulate matter is collected, thereby changing conductance between the first sensing electrode and the second sensing electrode. An ionic conductive material is in electrical communication with the first sensing electrode and the second sensing electrode.

The particulate matter sensor described herein allows for diagnostics to take place while minimizing manufacturing time and cost.

DETAILED DESCRIPTION OF INVENTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "left", "right", "horizontal", "vertical", "bottom", and "top" are used herein, unless otherwise noted, merely for convenience of description, and are not limited to any one position or spatial orientation. Finally, unless defined otherwise, technical and scientific terms used herein have the same meaning as is commonly understood by one of skill in the art to which this invention belongs.

Figure 1:
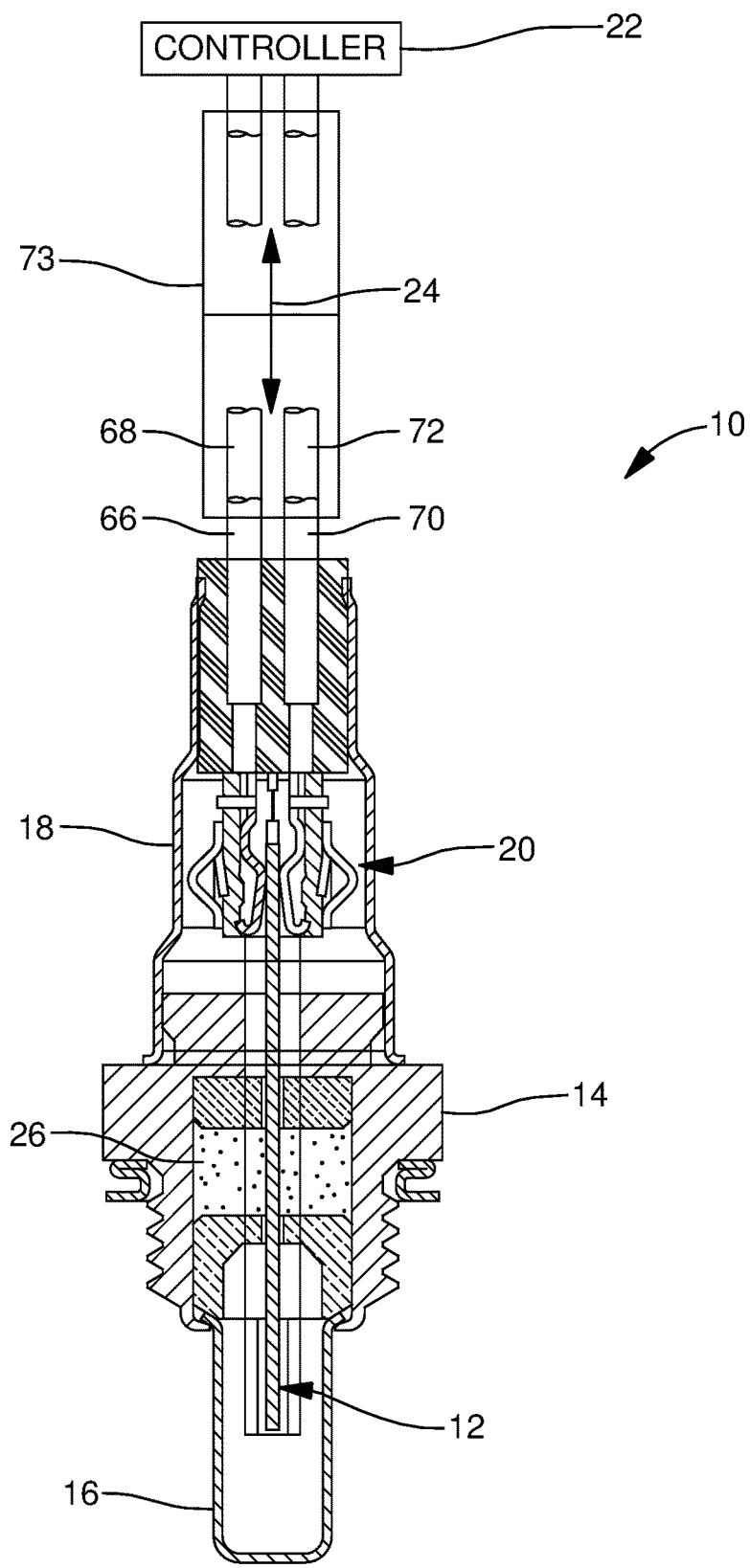
FIG. 1 is a cross-sectional view of a particulate matter sensor in accordance with the present disclosure.

In accordance with the present disclosure and referring initially to FIG. 1, a particulate matter sensor 10, shown in axial cross-section, is provided for detecting particulate matter, also known as soot, in a gas stream (not shown) for example, of exhaust from an internal combustion engine (not shown). Particulate matter sensor 10 generally includes a sensing element 12; a sensor shell 14 which supports sensing element 12 and which fixes particulate matter sensor 10 to a conduit (not shown) through which the gas stream passes; a lower shield 16 which protects the portion of sensing element 12 which extends into the conduit; an upper shield 18 which protects the portion of sensing element 12 which is outside of the conduit; and a connector assembly 20 which mates with sensing element 12 to provide electrical communication, as illustrated by bi-directional arrow 24, between sensing element 12 and a controller 22. In order to prevent the gas stream from migrating from lower shield 16 to upper shield 18, a gas seal 26 is provided in sensor shell 14 and may be, by way of non-limiting example only, talc or glass which sealingly mates with an outer periphery of sensing element 12 and sealingly mates with an inner periphery of sensor shell 14.

Figure 2:
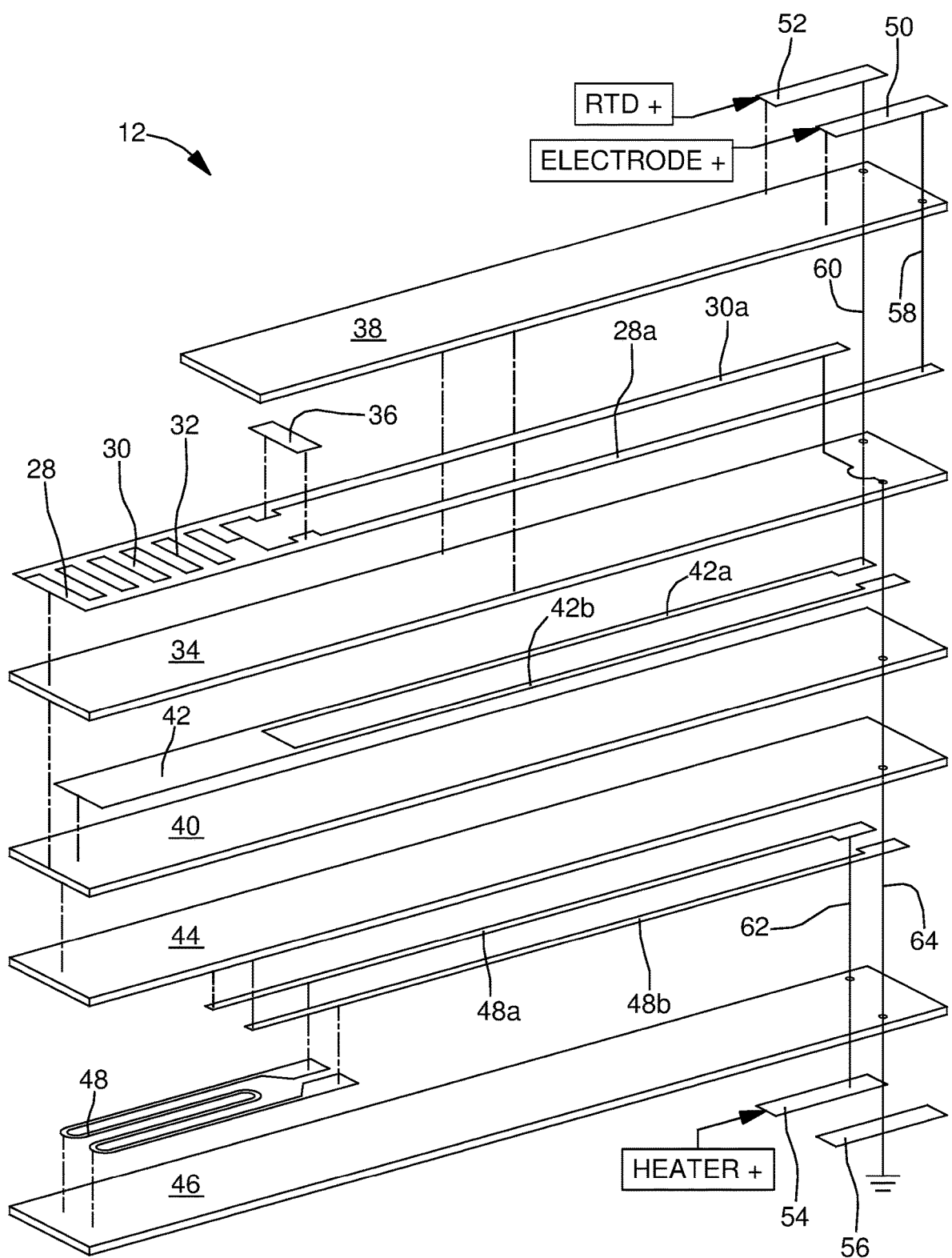
FIG. 2 is an exploded isometric view of a sensing element of the particulate matter sensor of FIG. 1.

Sensing element 12 will now be described in greater detail with respect to FIG. 2 which illustrates sensing element 12 exploded to show exemplary layers. In order to sense particulate matter, sensing element 12 includes a first sensing electrode 28 and a second sensing electrode 30 such that first sensing electrode 28 and second sensing electrode 30 are electrically isolated from each other in the absence of particulate matter such that an electrode gap 32 is formed therebetween. First sensing electrode 28 and second sensing electrode 30 are located within lower shield 16 which receives the exhaust stream. Consequently, particulate matter present in the exhaust stream accumulates on first sensing electrode 28 and second sensing electrode 30, thereby bridging electrode gap 32 and changing the conductance between first sensing electrode 28 and second sensing electrode 30 which allows the particulate matter to be quantified. As shown in the figures, first sensing electrode 28 and second sensing electrode 30 are illustrated in a pattern of interdigitized fingers, however, other patterns can be envisioned. First sensing electrode 28 includes a first sensing electrode lead 28a which extends into upper shield 18, and similarly, second sensing electrode 30 includes a second sensing electrode lead 30a which extends into upper shield 18. First sensing electrode lead 28a and second sensing electrode lead 30a provide for electrical connection between first sensing electrode 28 and connector assembly 20 and between second sensing electrode 30 and connector assembly 20. As embodied herein first sensing electrode 28 is the positive electrode and second sensing electrode 30 is the negative electrode as will be more clear later.

First sensing electrode 28, first sensing electrode lead 28a, second sensing electrode 30, and second sensing electrode lead 30a are disposed on a first sensor substrate 34 which is electrically insulative and non-ionically conducting, and may preferably be, by way of non-limiting example only, alumina, however, other exemplary materials may include alumina nitride, boron nitride, silica, molyte, and cordeorite. First sensor substrate 34 provides structure to support first sensing electrode 28, first sensing electrode lead 28a, second sensing electrode 30, and second sensing electrode lead 30a.

In order to provide diagnostic capability, an ionic conductive material 36 is provided in electrical communication with first sensing electrode 28 and second sensing electrode 30 such that the impedance of ionic conductive material 36 has an inverse relationship with temperature, i.e. impedance decreases as temperature increases and vice versa. Furthermore, the impedance of ionic conductive material 36 is effectively infinite, i.e. greater than 100 megaohms, at normal operating temperature, which is typically below 400° C., and the impedance of ionic conductive material 36 decreases to a predetermined value which may be, by way of non-limiting example only, 10 megaohms or less and may be 1 megaohm or less or 500 kiloohms or less, when elevated to a predetermined temperature above the normal operating temperature, i.e. above 400° C., which may be accomplished during regeneration of particulate matter sensor 10, i.e. when accumulated particulate matter is cleaned from the vicinity of first sensing electrode 28, second sensing electrode 30, and sensing electrode gap 32. As illustrated in FIG. 2, ionic conductive material 36 contacts first sensing electrode lead 28a and second sensing electrode lead 30a and provides a continuous bridge between first sensing electrode lead 28a and second sensing electrode lead 30a. Ionic conductive material 36 is located within lower shield 16 and may be, by way of non-limiting example only, partially stabilized zirconia, fully stabilized zirconia, doped alumina, doped high temperature glass, doped low temperature glass, or titanium oxide. Use of ionic conductive material 36 will be described in greater detail later.

A protective layer 38 is provided over at least a portion of first sensor substrate 34 such that first sensing electrode lead 28a, second sensing electrode lead 30a, and ionic conductive material 36 are located between protective layer 38 and first sensor substrate 34. Protective layer 38 provides protection to first sensing electrode lead 28a, second sensing electrode lead 30a, and ionic conductive material 36 from the exhaust stream for portions thereof which are located within lower shield 16. While protective layer 38 is illustrated as not extending over first sensing electrode 28 and second sensing electrode 30, it should be understood that protective layer 38 may alternatively extend over first sensing electrode 28 and second sensing electrode 30 and include a slot extending therethrough which is aligned with electrode gap 32 to expose electrode gap 32 to the exhaust stream, thereby allowing particulate matter to accumulate and bridge electrode gap 32.

A second sensor substrate 40 is located on the side of first sensor substrate 34 which is opposite protective layer 38 such that a resistance temperature detector (RTD) 42 is located between first sensor substrate 34 and second sensor substrate 40 and such that RTD 42 is located within lower shield 16. Second sensor substrate 40 is an electrically insulative material, which may be, by way of non-limiting example only, one of the materials described previously relative to first sensor substrate 34. Extending from RTD 42 is a first RTD lead 42a which is the positive lead as embodied herein and a second RTD lead 42b which is the negative lead as embodied herein such that first RTD lead 42a and second RTD lead 42b extend into upper shield 18. First RTD lead 42a and second RTD lead 42b provide for electrical connection between RTD 42 and connector assembly 20. RTD 42, first RTD lead 42a, and second RTD lead 42b may be, by way of non-limiting example only, a resistive platinum element, although other materials for RTD's are known to those skilled in the art. RTD 42 is used to detect the temperature of sensing element 12 which is used in control of particulate matter sensor 10.

In order to provide structural rigidity to sensing element 12, a third sensor substrate 44 may be provided on the side of second sensor substrate 40 which is opposite first sensor substrate 34. Third sensor substrate 44 is an electrically insulative material, and may be, by way of non-limiting example only, one of the materials described previously relative to first sensor substrate 34.

A fourth sensor substrate 46 is located on the side of third sensor substrate 44 which is opposite second sensor substrate 40 such that a heater 48 is located between third sensor substrate 44 and fourth sensor substrate 46 and such that heater 48 is located within lower shield 16. Fourth sensor substrate 46 is an electrically insulative material, which may be, by way of non-limiting example only, one of the materials described previously relative to first sensor substrate 34. Extending from heater 48 is a first heater lead 48a which is the positive lead as embodied herein and a second heater lead 48b which is the negative lead as embodied herein such that first heater lead 48a and second heater lead 48b extend into upper shield 18. First heater lead 48a and second heater lead 48b provide for electrical connection between heater 48 and connector assembly 20. Heater 48, first heater lead 48a, and second heater lead 48b may be, by way of non-limiting example only, platinum, although other materials for heaters are known to those skilled in the art. Heater 48 is positioned to elevate the temperature of first sensing electrode 28 and second sensing electrode 30 in order to clean accumulated particulate matter from the vicinity of first sensing electrode 28, second sensing electrode 30, and electrode gap 32 when the heater 48 is electrically powered by supplying current through first heater lead 48a and second heater lead 48b, thereby regenerating particulate matter sensor 10. Heater 48 is also positioned to elevate the temperature of ionic conductive material 36 in order to reduce the impedance of ionic conductive material 36 for use in diagnosing particulate matter sensor 10 as will be described in greater detail later.

In order to provide electrical connection between connector assembly 20 and sensing element 12, sensing element 12 includes a sensing electrode positive pad 50, an RTD positive pad 52, a heater positive pad 54, and a common ground pad 56 which are each made of an electrically conductive material, and may be, by way of non-limiting example only, platinum. Sensing electrode positive pad 50 is located on, and in contact with, the side of protective layer 38 which is opposite first sensor substrate 34 and is in electrical communication with first sensing electrode lead 28a by way of a first sensing electrode conductive path 58 which passes through a via formed in protective layer 38. RTD positive pad 52 is located on, and in contact with, the side of protective layer 38 which is opposite first sensor substrate 34 and is in electrical communication with first RTD lead 42a by way of a first RTD conductive path 60 which passes through vias formed in protective layer 38 and first sensor substrate 34. Heater positive pad 54 is located on, and in contact with, the side of fourth sensor substrate 46 which is opposite third sensor substrate 44 and is in electrical communication with first heater lead 48a by way of a first heater conductive path 62 which passes through a via formed in fourth sensor substrate 46. Common ground pad 56 is located on, and in contact with, the side of fourth sensor substrate 46 which is opposite third sensor substrate 44 and is in electrical communication with second sensing electrode lead 30a, second RTD lead 42b, and second heater lead 48b by way of a common ground conductive path 64 which passes through vias formed in first sensor substrate 34, second sensor substrate 40, third sensor substrate 44, and fourth sensor substrate 46.

Connector assembly 20 includes terminals with are each in electrical contact with a respective one of sensing electrode positive pad 50, RTD positive pad 52, heater positive pad 54, and common ground pad 56. Each terminal is also in electrical contact with a respective one of a plurality of wires, namely a sensing electrode positive wire 66, an RTD positive wire 68, a heater positive wire 70, and a common ground wire 72 which each extend to controller 22. In order to allow particulate matter sensor 10 to be connected and disconnected from controller 22, a sensor to controller connector 73 may be provided which allows sensing electrode positive wire 66, RTD positive wire 68, heater positive wire 70, and common ground wire 72 to be selectively connected and disconnected.

Figure 3:
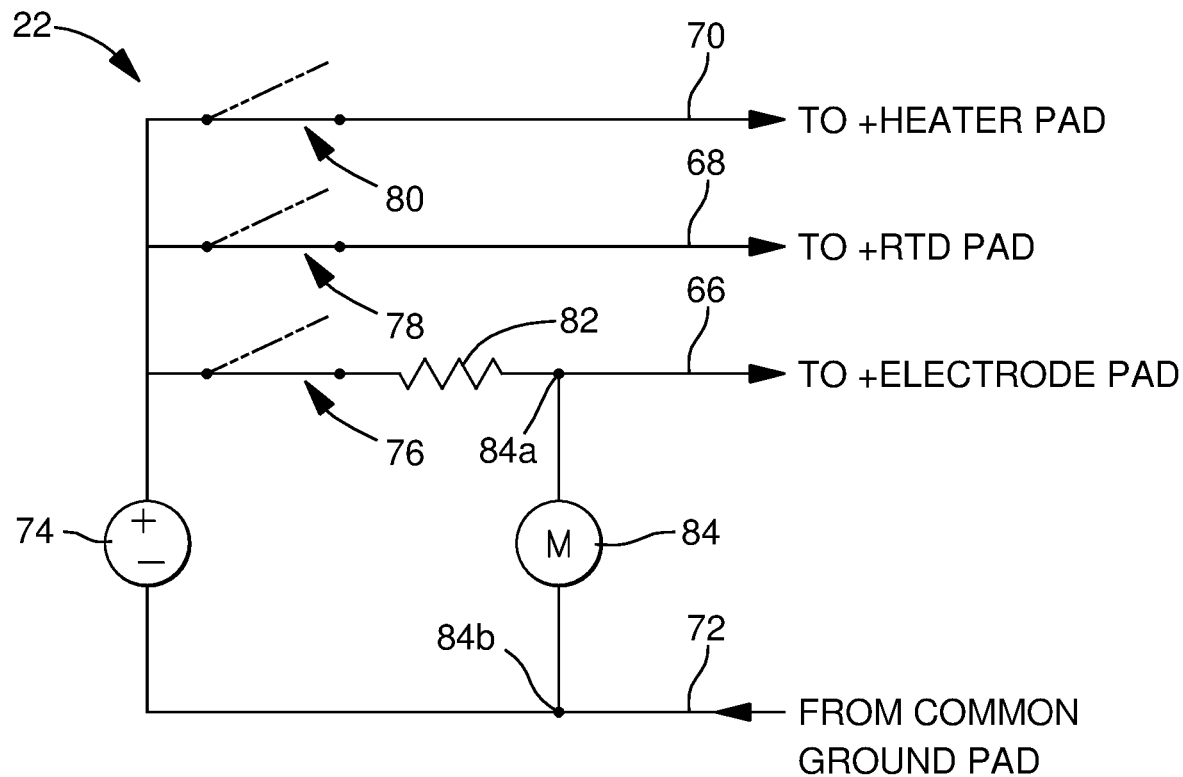
FIG. 3 is an electrical schematic of a controller for use with the sensing element.

As illustrated in FIG. 3, controller 22 includes a voltage supply 74 which is connected to first sensing electrode 28, second sensing electrode 30, RTD 42, and heater 48 by way of sensing electrode positive wired, RTD positive wire 68, heater positive wire 70, and common ground wire 72. A sensing electrode switch 76 (illustrated as closed with a solid line and illustrated as open with a phantom line) may be provided between voltage supply 74 and first sensing electrode 28 in order to selectively permit and prevent electrical communication between voltage supply 74 and first sensing electrode 28. An RTD switch 78 (illustrated as closed with a solid line and illustrated as open with a phantom line) may be provided between voltage supply 74 and first RTD lead 42a in order to selectively permit and prevent electrical communication between voltage supply 74 and first RTD lead 42a. A heater switch 80 (illustrated as closed with a solid line and illustrated as open with a phantom line) may be provided between voltage supply 74 and first heater lead 48a in order to selectively permit and prevent electrical communication between voltage supply 74 and first heater lead 48a.

In addition to the foregoing, controller 22 includes a pull-up resistor 82 having a resistance value $R_{pullup}$ and a voltage measurement means 84. Pull-up resistor 82 is connected electrically in series between sensing electrode switch 76 and sensing electrode positive pad 50 and voltage measurement means 84 is connected at a first junction 84a which is located between pull-up resistor 82 and sensing electrode positive pad 50 and at a second junction 84b between common ground pad 56 and voltage supply 74.

Under normal operation when soot is to be accumulated and measured, heater switch 80 remains open (illustrated by phantom line in FIG. 3), thereby causing heater 48 to be off and not produce heat which allows the portion of sensing element 12 which is located within lower shield 16 to remain no hotter than the temperature of the exhaust gases, i.e.

normal operating temperature, containing particulate matter to be sensed. As a result, the impedance of ionic conductive material 36 is effectively infinite. The resistance, $R_{sensor}$, resulting from the combination of impedance of ionic conductive material 36 and resistance due to the particulate matter accumulated across electrode gap 32 is represented as:

$$R_{sensor} = \frac{Z_{icm} \times R_{particulate}}{Z_{icm} + R_{particulate}}$$

where $Z_{icm}$ is the impedance of ionic conductive material 36 and $R_{particulate}$ is the resistance due to particulate matter accumulated across electrode gap 32. However, since $Z_{icm}$ is effectively infinite at this operational condition, $R_{sensor}$ is simply $R_{particulate}$ and the voltage measured by voltage measurement means 84 will be $$V_{measured} = V_{supply} \frac{R_{sensor}}{R_{pullup} + R_{sensor}}$$

where $V_{supply}$ is the voltage provided by voltage supply 74 and $R_{sensor}$ is as previously described.

After $R_{particulate}$ a has reached a predetermined threshold, a predetermined time has passed, or some other predetermined condition has been met, particulate matter sensor 10 is regenerated in order to remove accumulated particulate matter from the vicinity of first sensing electrode 28, second sensing electrode 30, and electrode gap 32. Regeneration is accomplished by closing heater switch 80 (illustrated in solid line in FIG. 3), thereby causing heater 48 to produce heat and remove the accumulated particulate matter. In addition to removing the particulate matter, heater 48 elevates the temperature of ionic conductive material 36, thereby causing the impedance of ionic conductive material 36 to fall. With the particulate matter removed and the impedance of ionic conductive material 36 decreased to a predetermined level, for example 10 megaohms, $R_{sensor}$ is now effectively equal to $Z_{icm}$ since $R_{particulate}$ is now effectively infinite. As a result, if the voltage measured by measurement means 84 is higher than the highest voltage that would be present in a properly connected and undamaged sensor (for example 91% of $V_{supply}$ with $R_{pullup}$=1 megaohm and $Z_{icm}$=10 megaohms) a fault condition can be concluded, namely an open circuit. In response to detection of a fault condition, appropriate action may be taken, for example, an indicator light may be actuated and/or an operating parameter of the engine or exhaust system may be adjusted.

Figure 4:
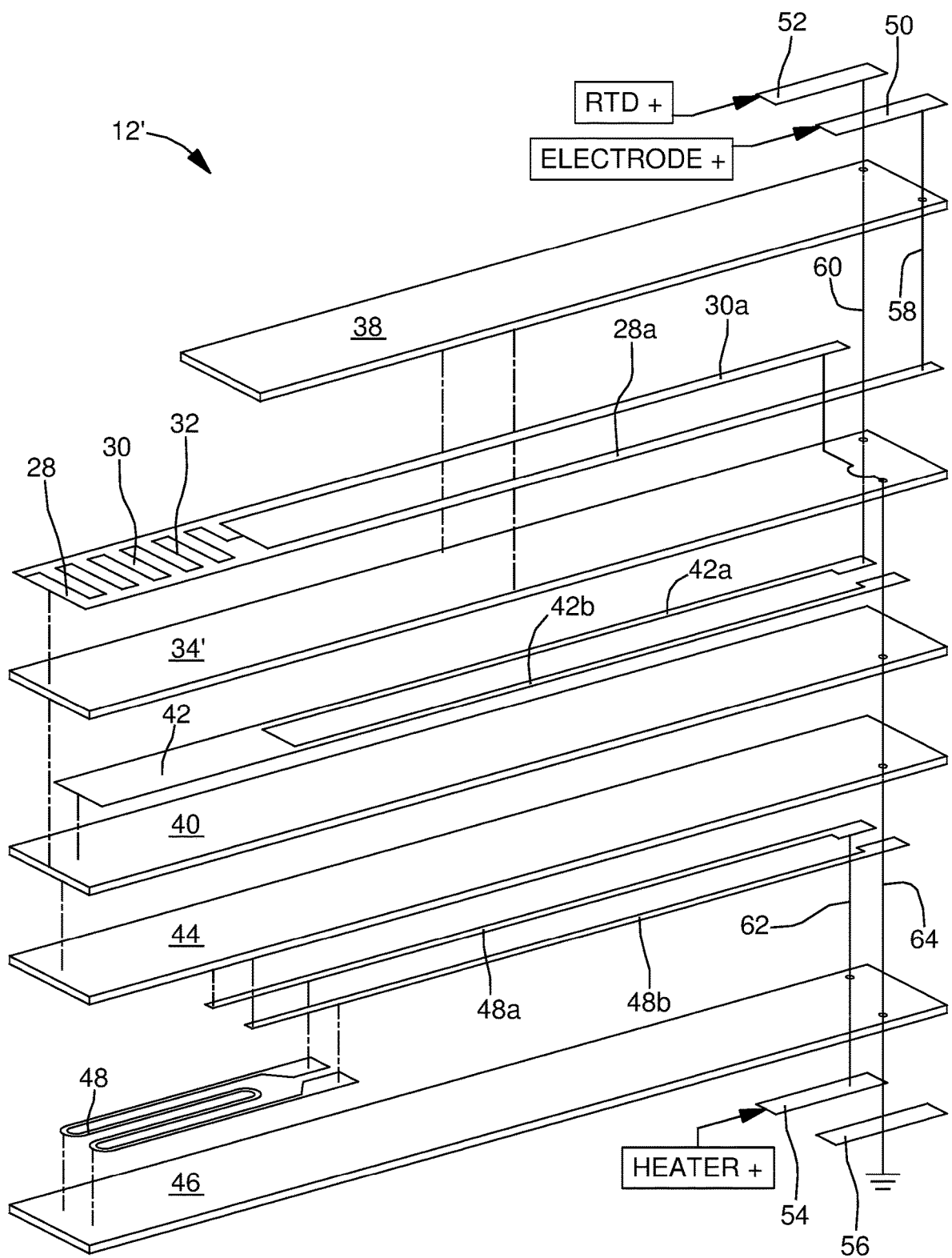
FIG. 4 is an exploded isometric view of another sensing element in accordance with the present disclosure.

Another sensing element 12' in accordance with the present disclosure is illustrated in FIG. 4. Sensing element 12' is similar to sensing element 12 and consequently only the differences will be described herein. The notable distinction of sensing element 12' from sensing element 12 is the implementation of ionic conductive material 36. In sensing element 12', first sensor substrate 34 is substituted with first sensor substrate 34' which is a base material doped to cause first sensor substrate 34' to be ionic conductive. Consequently, first sensor substrate 34' takes the place of ionic conductive material 36 of sensing element 12, and as a result, a separate material applied to the substrate and spanning across first sensing electrode lead 28a and second sensing electrode lead 30a is not needed. The base material may preferably be, by way of non-limiting example only, alumina, however, other exemplary materials may include alumina nitride, boron nitride, silica, molyte, and cordeorite and the dopant may be, by way of non-limiting example only, metals from the alkali or alkaline families, including, but not limited to sodium, calcium, lithium, and magnesium. Other materials for the dopant may include metals from the transition family such as ytrrium, zirconia, lanthanum, and cerium. The dopant may be provided in a concentration from ten to hundreds of parts per million and may be as much as a few thousand parts per million. Operation using sensing element 12' is the same as described previously with respect to sensing element 12 and may be carried out using controller 22 in the same manner.

Figure 5:
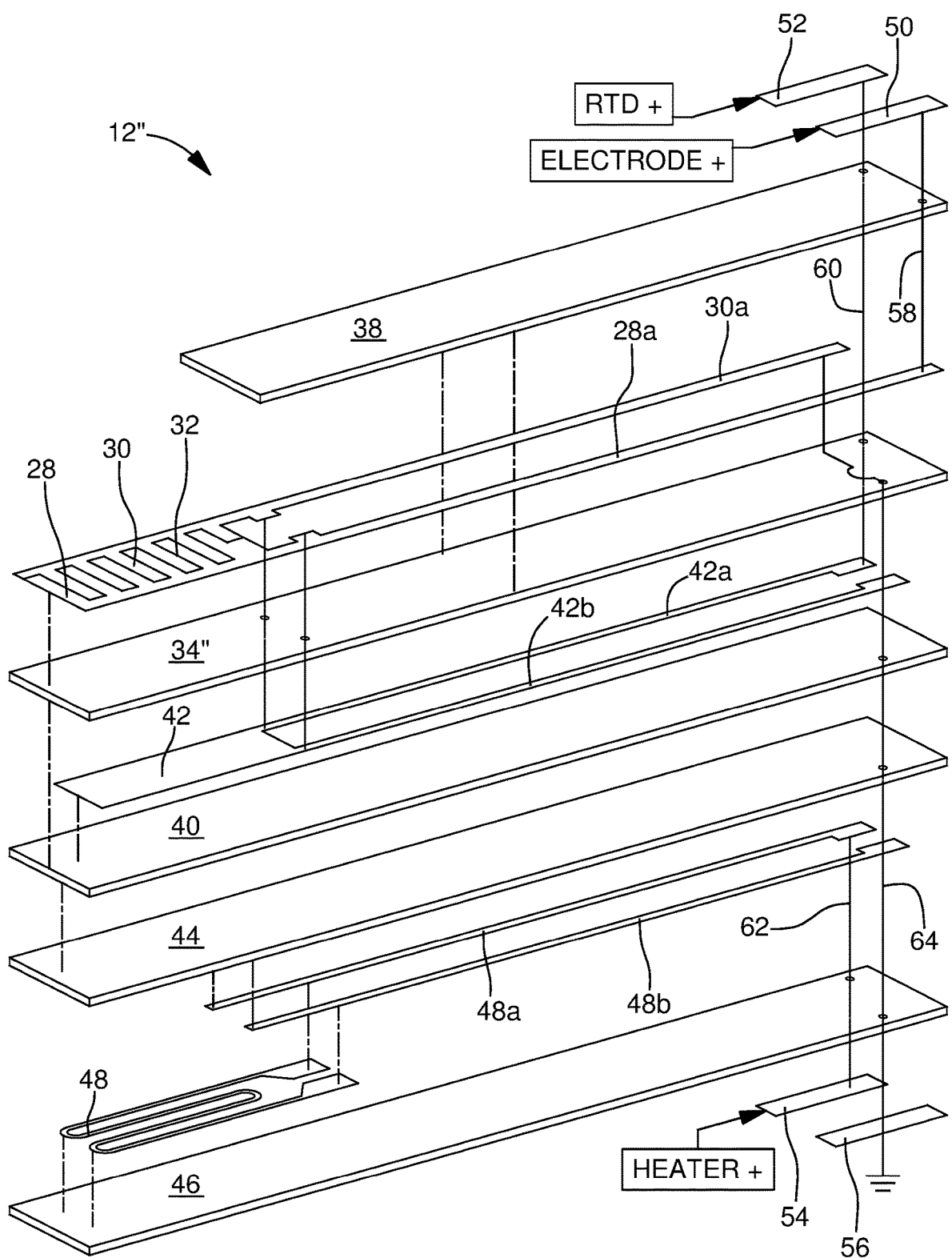
FIG. 5 is an exploded isometric view of another sensing element in accordance with the present disclosure.
Figure 7:
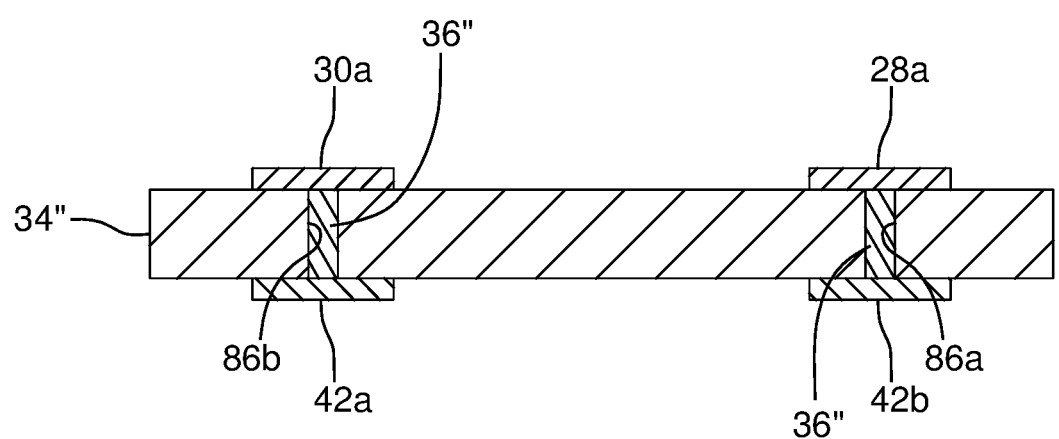
FIG. 7 is a cross-sectional view of a portion of the sensing element of FIG. 5.

Another sensing element 12" in accordance with the present disclosure is illustrated in FIGS. 5 and 7. Sensing element 12" is similar to sensing element 12 and consequently only the differences will be described herein. The notable distinction of sensing element 12' from sensing element 12 is the implementation of ionic conductive material 36. In sensing element 12", first sensor substrate 34 is replaced with first sensor substrate 34" which is electrically insulative and non-ionically conducting and which includes vias 86a, 86b extending therethrough between first sensing electrode lead 28a and second RTD lead 42b and between second sensing electrode lead 30a and first RTD lead 42a respectively. Ionic conductive material 36" is placed in vias 86a, 86b such that ionic conductive material 36" in via 86a is in electrical communication with first sensing electrode lead 28a and second RTD lead 42b and ionic conductive material 36" in via 86b is in electrical communication with second sensing electrode lead 30a and first RTD lead 42a. Ionic conductive material 36" includes the same properties described previously with respect to ionic conductive material 36 and may be one of the exemplary materials provided with respect to ionic conductive material 36.

Figure 6:
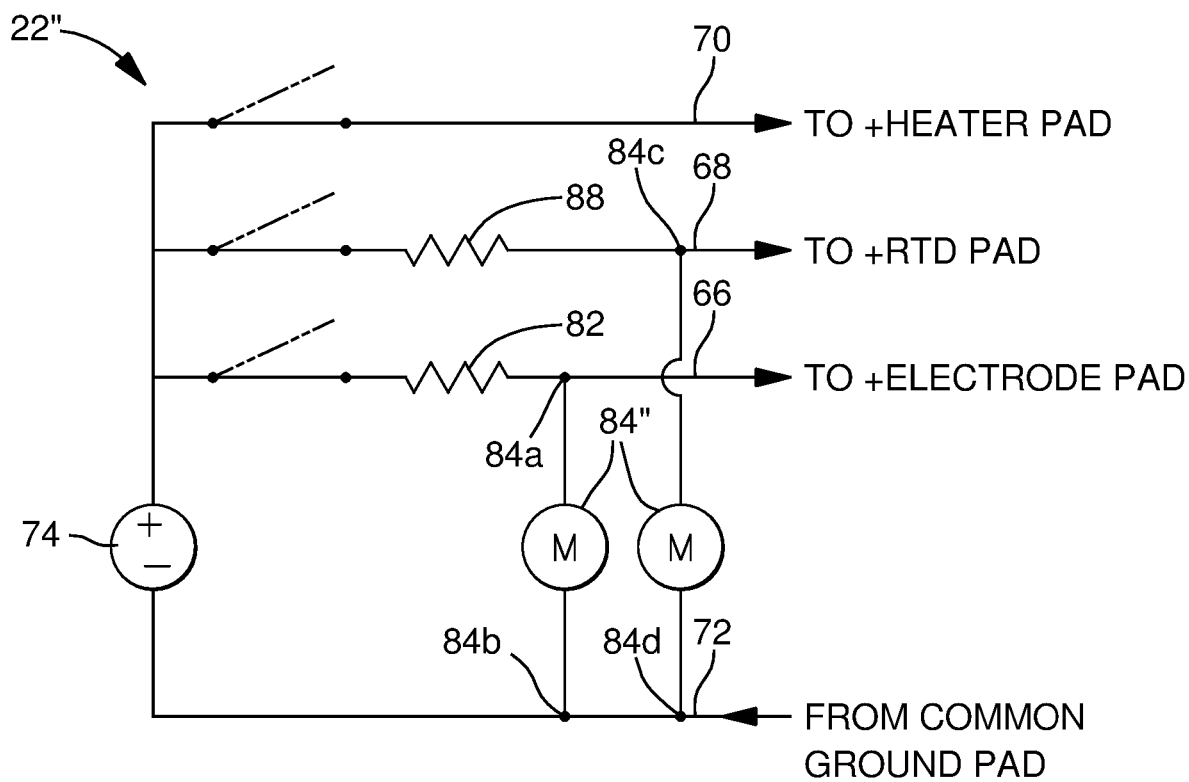
FIG. 6 is an electrical schematic of a controller for use with the sensing element of FIG. 5.

The principle of operation of sensing element 12" to diagnose an open circuit is the same as described with respect to sensing element 12, however, requires that first sensing electrode 28/first sensing electrode lead 28a and second sensing electrode 30/second sensing electrode lead 30a be evaluated independently. As a result, a variation to controller 22 is required which is exemplified in FIG. 6 as controller 22". Controller 22" is similar to controller 22, except controller 22" includes a second pull-up resistor 88 having a resistance value $R_{pullup2}$ and a voltage measurement means 84" is substituted for voltage measurement means 84. Second pull-up resistor 88 is connected electrically in series between RTD switch 78 and RTD positive pad 52. Voltage measurement means 84" includes one section connected at first junction 84a which is located between pull-up resistor 82 and sensing electrode positive pad 50 and at second junction 84b which is located between common ground pad 56 and voltage supply 74 and also includes a second section connected at a third junction 84c which is located between second pull-up resistor 88 and RTD positive pad 52 and at a fourth junction 84d which is located between common ground pad 56 and voltage supply 74. While FIG. 6 illustrates voltage measurement means 84" as including two discrete meters, it should be understood that a single meter could be used in connection with one or more switches which allows the single meter to be switched between the positive electrode branch and the positive RTD branch.

After particulate matter accumulation has reached a predetermined threshold, regeneration is carried out in order to remove accumulated particulate matter from the vicinity of first sensing electrode 28 and second sensing electrode 30 and spanning electrode gap 32. Regeneration is accomplished by closing heater switch 80 (illustrated in solid line in FIG. 6), thereby causing heater 48 to produce heat and remove the accumulated particulate matter. In addition to removing the particulate matter, heater 48 elevates the temperature of ionic conductive material 36″, thereby causing the impedance of ionic conductive material 36″ to fall. Unlike sensing element 12 and sensing element 12′ which use the lowered impedance of ionic conductive material 36 and first sensor substrate 34′ (which is an ionic conductive material) across first sensing electrode lead 28a and second sensing electrode lead 30a for diagnosis, sensing element 12″ uses the lowered impedance of ionic conductive material 36″ across first sensing electrode lead 28a and second RTD lead 42b and the lowered impedance of ionic conductive material 36″ across second sensing electrode lead 30a and first RTD lead 42a for diagnosis. More specifically, if the voltage measured between first junction 84a and second junction 84b is higher than the highest voltage that would be present in a properly connected and undamaged sensor (for example 91% of $V_{supply}$ with $R_{pullup}=1$ megaohm and $Z_{icm}=10$ megaohms) a fault condition can be concluded, namely an open circuit. Similarly, if the voltage measured between third junction 84c and fourth junction 84d is higher than the highest voltage that would be present in a properly connected and undamaged sensor (for example 91% of $V_{supply}$ with $R_{pullup2}=1$ megaohm and $Z_{icm}=10$ megaohms) a fault condition can be concluded, namely an open circuit. In response to detection of a fault condition, appropriate action may be taken, for example, an indicator light may be actuated and/or an operating parameter of the engine or exhaust system may be adjusted.

Sensing elements 12, 12′, 12″ may be formed by providing the substrates, protective layer, and ionic conductive materials individually using conventional techniques such as tape casting. The conductive features, e.g. pads, leads, electrodes, RTD, and heater, may be deposited using conventional techniques such as using ink paste applied via sputtering, screen printing, lamination, stenciling or the like. The various layers in a green state together with the conductive features are brought together and sintered as a single unit to complete sensing elements 12, 12′, 12″ which are ceramic elements.

By using ionic conductive materials 36, 34′, 36″ as described herein, diagnosis of particulate matter sensor 10 is permitted while shortening manufacturing time and reducing manufacturing costs since ionic conductive materials 36, 34′, 36″ can be sintered together with the remaining portions of sensing elements 12, 12′, 12″.

While the embodiments of a particulate matter sensor that facilitates diagnosis of fault conditions have been shown and described in detail, it is to be understood that the subject matter which is encompassed by the present invention is limited only by the following claims.

We claim:

1. A particulate matter sensor for detecting particulate matter in a gas stream, said particulate matter sensor comprising:
   a first sensing electrode;
   a second sensing electrode spaced away from said first sensing electrode such that an electrode gap is formed between said first sensing electrode and said second sensing electrode upon which particulate matter is collected, thereby changing conductance between said first sensing electrode and said second sensing electrode; and
   an ionic conductive material in electrical communication with said first sensing electrode and said second sensing electrode.

2. A particulate matter sensor as in claim 1, further comprising a substrate, wherein said first sensing electrode and said second sensing electrode are supported by said substrate on a first side of said substrate.

3. A particulate matter sensor as in claim 2, wherein said substrate is said ionic conductive material.

4. A particulate matter sensor as in claim 3, wherein said substrate is a base material with a dopant.

5. A particulate matter sensor as in claim 4, wherein said base material is alumina.

6. A particulate matter sensor as in claim 4, wherein said dopant is a metal from the group consisting of the alkali family, the alkaline family, and the transition family.

7. A particulate matter sensor as in claim 2, wherein:
   said substrate is electrically insulative and non-ionically conducting; and
   said ionic conductive material is disposed on said substrate such that said ionic conductive material provides a continuous bridge between said first sensing electrode and said second sensing electrode.

8. A particulate matter sensor as in claim 7, wherein said ionic conductive material comprises zirconia.

9. A particulate matter sensor as in claim 2, wherein:
   said particulate matter sensor further comprises a temperature sensor on a side of said substrate which is opposite said first sensing electrode and said second sensing electrode, said temperature sensor having a positive temperature sensor lead and a negative temperature sensor lead extending therefrom;
   said substrate is electrically insulative and non-ionically conducting and includes a first via and a second via each extending therethrough;
   said ionic conductive material is located in said first via and said second via such that said ionic conductive material in said first via is in electrical communication with said first sensing electrode and said positive temperature sensor lead and such that said ionic conductive material in said second via is in electrical communication with said second sensing electrode and said negative temperature sensor lead.

10. A particulate matter sensor as in claim 1, wherein said ionic conductive material has an inverse relationship between temperature and impedance.

11. A particulate matter sensor as in claim 10, wherein said ionic conductive material has an impedance which is effectively infinite at temperatures below 400° C.

12. A particulate matter sensor as in claim 11, wherein said ionic conductive material has an impedance which is less than or equal to 100 megaohms when at a predetermined temperature which is greater than or equal to 400° C.

13. A particulate matter sensor as in claim 12 further comprising a heater configured to heat said ionic conductive material to said predetermined temperature.

* * * * *